United States Patent [19]

Castillo

[11] Patent Number: 5,993,836
[45] Date of Patent: Nov. 30, 1999

[54] TOPICAL ANESTHETIC FORMULATION

[76] Inventor: James G. Castillo, 15412-15$^{th}$St., Lutz, Fla. 33549

[21] Appl. No.: 09/067,948

[22] Filed: Apr. 28, 1998

[51] Int. Cl.$^6$ ................................. A61K 6/00; A61K 7/00
[52] U.S. Cl. ......................... 424/401; 424/443; 424/435; 424/485
[58] Field of Search ................................. 424/401, 443, 424/435, 485, 484, 450, 486

[56] References Cited

U.S. PATENT DOCUMENTS

| | | | |
|---|---|---|---|
| 4,529,601 | 7/1985 | Broberg et al. | 514/626 |
| 4,562,060 | 12/1985 | Broberg et al. | 424/28 |
| 5,002,974 | 3/1991 | Geria | 514/782 |
| 5,332,576 | 7/1994 | Mantelle | 424/443 |
| 5,585,398 | 12/1996 | Ernst | 514/537 |

*Primary Examiner*—Thurman K. Page
*Assistant Examiner*—William E. Benston, Jr.
*Attorney, Agent, or Firm*—Pendorf & Cutliff

[57] ABSTRACT

A topical, transdermal anesthetic comprising a eutectic mixture of, preferably, lidocaine and prilocaine in a ratio of about 3:1 by weight, incorporated within a lipophilic base. In addition to the property of rapid-onset, the formulation of the present invention has high storage stability and is less restricted by dosage limitations of other prilocaine-containing transdermal anesthetics and is, advantageously, not dependent upon occlusive dressing for optimal transdermal absorption.

20 Claims, No Drawings

TOPICAL ANESTHETIC FORMULATION

BACKGROUND OF THE INVENTION

1. Field of the Invention

This invention relates to a new formulation of a topical anesthetic and, more particularly, to a fast acting transdermal, topical anesthetic formulation having improved stability.

2. Description of the Related Art

Surgical techniques such as cosmetic resurfacing involving surgical ablation with an Erbium:YAG laser, and other laser procedures involving vaporization, excision, incision, and coagulation of soft tissue in medical specialties including dermatology, plastic surgery, podiatry, neurosurgery, gynecology, otorhinolaryngology (ENT), arthroscopy (knee surgery), and invasive and endoscopic general surgery, can only be performed after the highly sensitive nerve endings in the skin are anesthetized. The preferred method of administration of anesthetic is transdermally.

Skin, however, is a formidable barrier to the absorption of analgesics. Because the skin must serve as a barrier to the ingress of pathogens and toxic materials, and the egress of physiologic fluids, the skin is highly impermeable. Impermeability allows the skin to preserve its own integrity while simultaneously maintaining the delicate dynamic electrolyte balance of the body. Therefore, the skin functions both as a containment mechanism and as a microbial, chemical, radiation and thermal barrier.

This impermeability may be attributed to the nature of one very thin layer created by normal development and physiological changes in the skin. After cells are formed in the basal layer, they begin to migrate toward the skin surface, until they are eventually sloughed off. As they undergo this migration, they become progressively more dehydrated and keratinized. When they reach the surface, just prior to being discarded, they form a thin layer of dense, metabolically inactive cells approximately ten microns (10-15 cells) thick, the stratum corneum or "cornified layer". As a result of the high degree of keratinization of the cells which comprise the stratum corneum, a formidable barrier is created. Absorption through a mucosal surface is generally efficient because the stratum corneum is absent. Therefore, any formulation to be utilized as an efficient topical, transdermal anesthetic must be capable of being readily absorbed through the skin.

In addition to the thickness and integrity of the stratum corneum epidermis, percutaneous or transdermal absorption can significantly alter drug kinetics and depends on a variety of factors including site of application, size of active drug molecule, permeability of the membrane of the transdermal drug delivery system, state of skin hydration, pH of the drug, drug metabolism by skin flora, lipid solubility, and alteration of blood flow in the skin by additives and body temperature.

Certainly, it is well known to use topical, transdermal anesthetics, in dental applications such as in applying an anesthetic to the gum prior to injecting anesthetic. In mucous membranes, such as the lining of the mouth, topical anesthetics are readily absorbed and work well. However, on skin, the mechanics and physiology of absorption are much different.

Transdermal anesthetics are also useful for numbing an area prior to venipuncture, such as blood drawing. Pain relief is especially important in the area of pediatrics, where even minimal pain may result in an anxious and uncooperative patient.

In addition to its advantages over intravenous delivery, other advantages of transdermal delivery include avoidance of risks associated with parenteral treatment, elimination of the inconveniences of parenteral treatment; and elimination of gastrointestinal irritation resulting from exposing the gastrointestinal tract to pharmaceutical actives, preservatives, tableting agents, and the like.

In the past, several types of topical anesthetic methodology have been tried, including freezing the skin. This is done most easily by applying ice or spraying the skin with a vapocoolant, a chemical which evaporates quickly. This then freezes the surface of the skin. An example of this is ethyl chloride (chloroethane). Unfortunately, ethyl chloride has many disadvantages. It is difficult to numb large areas with these methods and the effect is short-lived, rarely lasting more than a few seconds to a minute. Further, ethyl chloride is flammable and, when used to produce local freezing, adjacent skin areas must be protected by application of petrolatum. Finally, the thawing process may be painful, and freezing may lower local resistance to infection and delay healing.

Cocaine solutions are also known, and act by blocking the initiation or conduction of the nerve pulse. For example, TAC (a mixture of tetracaine, adrenaline and cocaine) essentially eliminates pain and increases hemostasis during suturing of an open laceration but is not effective on unbroken skin. Further, system levels of cocaine have been documented after simple application of TAC soaked-pledgets to an open wound, thus, emphasizing the need for calculating and the limiting the dose of cocaine administered. Strict limitation of the total dose of each component according to the patient's lean body weight is crucial. As with any narcotic, the potential exists for respiratory depression and oxygen desaturation with the moderately rapid absorption through any mucosa.

Lidocaine is highly effective and is the most commonly used local anesthetic in the United States, especially in the form of aqueous solutions of lidocaine hydrochloride (Xylocaine®), which are administered intravenously through either direct injection or continuous infusion. Lidocaine stabilizes the neuronal membrane by inhibiting the ionic fluxes required for the initiation and conduction of impulses thereby effecting local anesthetic action. Lidocaine is also formulated as a jelly (Xylocaine® 2%), ointment, and spray for use as an anesthetic. Unfortunately, these formulations are only effectively absorbed through mucosal surfaces, not the skin.

A more recently developed transdermal anesthetic that utilizes lidocaine is EMLA® cream (Eutectic Mixture of Local Anesthetics), which patients have found preferable to lidocaine infiltration or ethyl chloride spray. EMLA® is an oil-in-water emulsion in which the oil phase is a eutectic mixture of lidocaine and prilocaine in a ratio of 1:1 by weight (2.5% and 2.5%, respectively), and comprising 92% purified water. A eutectic mixture is a mixture that has a melting point lower than that of its ingredients; therefore these two anesthetics after being heated and mixed exist as a liquid oil at room temperature, rather than as crystals. EMLA® cream is described in U.S. Pat. Nos. 4,529,601 (Broberg, et al.) and 4,562,060 (Broberg, et al.), which teach the mixing of specific proportions of certain local anesthetic agents in the form of their base in order to form a homogenous oil having a melting point below 40° C., preferably below 25° C.

Like lidocaine, prilocaine is an amide-type local anesthetic agent. Amides, are favorable as anesthetic agents, as opposed to esters, which are more sensitizing and can produce redness, swelling, irritation, itching, and other reactions. Unfortunately, methemoglobinaemia and cyanosis appear to occur more frequently with prilocaine than with other local anesthetics. Methemoglobinaemia describes the formation of oxidized iron compound in the heme protein of the red blood cell. It is a disease state of the erythrocyte. Cellular oxidant stress causes a structural change in the hemogloblin. If the oxidant stress is too great, methemoglobin levels rise and erythrocyte function is compromised. Symptoms usually occur when doses of prilocaine hydrochloride exceed about 8 mg per kg body-weight but the very young may be more susceptible. For the average person of 70 kg, this represents a dose of 560 mg. This severely limits the size of the area to be anesthetized.

A major inconvenience with EMLA® is that local anesthesia of intact skin is not achieved until at least 60 minutes following application. For more invasive procedures, such as split skin graft harvesting, at least two hours may be required. This delay in onset is a significant disadvantage, as it is a great inconvenience for both patients and medical staff. Such delay is particularly a problem in the area of pediatrics, where any additional time spent awaiting treatment only contributes to the anxiety of the patient.

Another disadvantage with EMLA® cream is that, for deep penetrative effect, it is necessary that the cream be applied under an occlusive dressing. Specifically, a bilayer of laminate and absorbent cellulose is taped to the area of the skin to be anesthetized. Such a dressing is inconvenient and messy.

It would be desirable, therefore, to have a topical, transdermal anesthetic which derives the benefits of both lidocaine and prilocaine, but which is free of all the above-described problems associated therewith.

Accordingly, it is an object of the present invention to provide a topical, transdermal anesthetic utilizing prilocaine, without such pronounced dosage limitations characteristic of other prilocaine-containing anesthetics.

Another object of the present invention is to provide a topical, transdermal anesthetic which exhibits comparably rapid onset.

Yet another object of the present invention is to provide a topical, transdermal anesthetic which is not dependent upon occlusive dressing for rapid absorption through the skin.

SUMMARY OF THE INVENTION

It has now been surprisingly discovered that by incorporating a specified concentration and ratio of a eutectic mixture comprising specified proportions of lidocaine and prilocaine in a lipophilic base, a transdermal anesthetic formulation is produced which has significantly more rapid onset than comparable transdermal anesthetics, such as EMLA® cream. For example, when applied to the face prior to surgical ablation, such as resurfacing with an Erbium:YAG laser, the anesthetic of the present invention works in as little as 10 to 40 minutes without occlusion. In addition to ablation, the present formulation is particularly useful prior to laser procedures requiring vaporation, excision, incision, and coagulation of soft tissue in medical specialties including dermatology, plastic surgery, podiatry, neurosurgery, gynecology, otorhinolaryngology (ENT), arthroscopy (knee surgery), and invasive and endoscopic general surgery.

It has further been surprisingly discovered that by using a lipophilic vehicle rather than an oil-in-water delivery system, the formulation is markedly improved in stability.

In a preferred embodiment, the present invention is directed to a topical, transdermal anesthetic preparation comprising (with all percentages being by weight):

about 10–20%, preferably about 15% lidocaine;
about 1–5%, preferably about 5% prilocaine;
about 0.0–1.0%, preferably about 0.75% dibucaine;
about 0.0–2.0%, preferably 0.5–1.0%, as effective for local vasoconstriction, of a sympathomimetic amine, preferably phenylephrine; and
the balance being a lipophilic base;
wherein the lidocaine and prilocaine are in the form of a eutectic mixture in a ratio of from a weight ratio of from about 15:1 to about 2:1.

In a particularly preferred embodiment of the invention, the ratio of lidocaine to prilocaine is from 8:1 to 2:1, most preferably about 3:1. While the recited analgesics are preferred, certain substitutions may be permissible.

In the present invention, phenylephrine preferably serves as a vasoconstrictor to facilitate localization of the effect. Other sympathomimetic amines that may be utilized will be described hereinafter.

Accordingly, the lipophilic based formulation of the present invention is one which contains no, or substantially no, aqueous component or aqueous functional-equivalent. Further, for the purposes of the present invention, the definition of lipophilic base is not particularly limited, and any of those known in the pharmaceutical and cosmetic industries may be employed, and includes lipophilic materials modified with thickeners, thinners, stabilizers, surfactants, etc.

Besides the above-described preferred embodiment, one may employ alternative formulations comprising a eutectic mixture of:

at least one pharmaceutically active anesthetic selected from a first group consisting of lidocaine, benzocaine, bupivacaine, dibucaine, mepivacaine, etidocaine, tetracaine, butanilicaine and trimecaine; and at least one pharmaceutically active anesthetic selected from a second group consisting of prilocaine, tetracaine, butanilicaine and trimecaine;

wherein the anesthetic(s) selected from the first group differ from the anesthetic(s) selected from the second group, in a weight ratio of anesthetic from the first group to anesthetic of the second group of from about 15:1 to about 2:1, in a lipophilic base. Preferably, at least one of said anesthetics is selected from the group consisting of prilocaine and lidocaine.

In addition to the rapid-onset property, the formulation of the present invention is free of the pronounced dosage limitations of other prilocaine-containing transdermal anesthetics. Further, the formulation is, advantageously, not dependent upon occlusive dressing for optimal transdermal absorption.

The present formulation may be used in lieu of infiltration anesthetics for minor procedures, or in conjunction with such anesthetics for more invasive procedures. Cosmetic applications include, but are not limited to laser resurfacing, electrolysis, permanent makeup application, body piercing, and tattooing. In addition to being used as preemptive anesthesia, the formulation may also be utilized in post-operatory pain relief therapy, especially in pediatrics and overly emotional patients.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other anesthetic formulations. It should also be realized by those skilled in the art that such equivalent formulations do not depart from the spirit and scope of the invention set forth in the appended claims.

DETAILED DESCRIPTION OF THE INVENTION

An advantage, as well as a major distinguishing feature, of the formulation of the present invention is attributable first to the eutectic mixture of the two preferred anesthetic agents, lidocaine and prilocaine, in the respective proportionate ratio of approximately 15:1 to 2:1 by weight; second, in the amount of the eutectic mixture in the lipophilic vehicle; and thirdly, in the utilization of a lipophilic base rather than an aqueous vehicle or an oil-in-water emulsion (the term "water", when referring to oil-in-water emulsions, includes hydrophilic liquids which serve as water substitutes).

The formulation of the present invention preferably contains from 10% to 20% by weight lidocaine and 1% to 5% by weight prilocaine based upon the total weight of formulation. Preferably, the formulation contains about 20% by weight lidocaine and about 5% by weight prilocaine.

The present lipophilic based formulation exhibits superior properties, including accelerated rate of onset, lack of pronounced dosage-limitations normally characteristic of other prilocaine transdermal anesthetics, and no dependency upon occlusive dressing for optimum transdermal absorption.

As lipophilic base, the present invention is not particularly limited, and any of those known in the pharmaceutical and cosmetic industries may be employed, and includes lipophilic materials modified with thickeners, thinners, stabilizers, surfactants, etc. As lipophilic materials an oleaginous material such as petrolatum, mineral oil thickened or gelled with polyethylene, high molecular weight paraffin waxes, mono and diglycerides of fatty acids gelled with high molecular weight fatty acids or polyamide complex of hydroxystearate, propylene glycol isostearate or isostearyl alcohol gelled with high molecular weight fatty acids and mixtures thereof may be used.

The lipophilic base should satisfy the following characteristics:

the base must allow the oils, and particularly the eutectic mixture, to be completely miscible therein;

the base must be compatible with the skin with the least possible number of adverse reactions;

the base must be smooth and pliable with no adverse odor;

the base should have a color appealing to the consumer;

the base must be stable and must provide a stable vehicle for the medication;

the base should be hydrophobic, i.e., have a low water absorbing capacity; and the base should be able to readily release the medication incorporated therein into the skin.

Preferably, the lipophilic component is a higher aliphatic alcohol, preferably of 8–18 carbon atoms, or an ester thereof. Examples of oleagenous (lipophilic) ointment bases include White Ointment USP, Yellow Ointment NF, Oleic Acid USP, Olive Oil USP, Paraffin USP, Petrolatum NF, White Petrolatum USP, Spermaceti Wax USP, Synthetic Spermaceti NF, Starch Glycerite NF, White Wax USP, and Yellow Wax USP. Lidocaine is chemically designated as an acetamide, 2-(diethylamino)-N(2,6-dimethylphenyl) and has an octanol:water partition ratio of 43 at pH 7.4. Prilocaine is chemically designated as a propanamide, N-(2-methyl-phenyl)-2-(propylamino) and has an octanol:water partition ratio of 25 at pH 7.4. As previously described, it is preferable that lidocaine and prilocaine exist in the formulation as an eutectic mixture in the ratio of about 3:1.

When applied to intact skin, the formulation of the present invention provides dermal analgesia by the release of lidocaine and prilocaine from the formulation into the epidermal and dermal layers of the skin and the accumulation of lidocaine and prilocaine in the vicinity of dermal pain receptors and nerve endings. Lidocaine and prilocaine are amide-type local anesthetic agents. Both lidocaine and prilocaine stabilize neuronal membranes by inhibiting the ionic fluxes required for the initiation of and conduction of impulses, thereby effecting local anesthetic action.

As a eutectic mixture, both anesthetics remain liquid at room temperature and the penetration and subsequent systemic absorption of both prilocaine and lidocaine are enhanced over that which would be seen if each component in crystalline form was applied separately. The dose of the present formulation which provides effective analgesia depends in part on the duration of the application over the treated area.

At least one sympathomimetic amine is preferably added to the formulation for its ability to mimic stimulation of the sympathetic nervous system. Specifically, when used with topical anesthetics, such amines act as vasoconstrictors to limit the locality of the anesthetic effect. Sympathomimetic amines that may be used in the preparation of the present invention include, but are not limited to, adrenaline, amezinium metilsulphate, cinnamedrine, clonazoline, clorprenaline, coumazoline, cyclopentamine, dimepropion, dimetofrine, dipivefrine, ephedra, ephedrine, etilefrine, fenoxazoline, hydroxyamphetamine, hydroxyephedrine, indanazoline, isometheptene, levonordefrin, mephentermine, metaraminol, methoxamine, methylephedrine, midodrine, naphazoline, noradrenaline acid, norfenefrine, octodrine, octopamine, oxedrine, oxilofrine, oxymetazoline, phenylephrine, phenylpropanolamine, prednazoline, psuedoephedrine, tefazoline, tetrahydrozoline, tramazoline, tuaminoheptane, tymazoline, and xylometazoline.

It is also preferable that the formulation comprise about 75% dibucaine. The formulation remains effective with a dibucaine content between 0.0% and 1.0%, however.

In addition to the above-described preferred embodiment, which contains lidocaine and prilocaine, alternative embodiments include all formulations comprising a eutectic mixture of at least one first pharmaceutically active anesthetic selected from the group consisting of benzocaine, lidocaine, bupivacaine, dibucaine, mepivacaine, etidocaine, tetracaine, butanilicaine and trimecaine and at least one second pharmaceutically active anesthetic selected from the group consisting of prilocaine, tetracaine, butanilicaine and trimecaine, said first and second pharmaceutically active agents present in a weight ratio of from about 15:1 to about 2:1 in a lipophilic base, and said anesthetic(s) selected from the first group differing from the anesthetic(s) selected from the second group, and at least one of said anesthetics preferably being either prilocaine or lidocaine.

In addition, the formulation of the present invention may be applied to a carrier of paper, patches, or pads, as disclosed in U.S. Pat. Nos. 4,529,601 (Broberg, et al.) and 4,562,060 (Broberg, et al.), so that the cellulose fibers of the preformed carrier is soaked with the formulation. Also, the present formulation may be prepared as a stick formulation suitable for delivery of pharmacologically-active compounds, as disclosed in U.S. Pat. No. 5,622,993 (McGinity, et al.).

The present invention will in the following be described more in detail with reference to a number of examples.

EXAMPLE 1

The formulation according to the invention was made in the following manner (total quantity: 800 g):

a) 50 g of prilocaine were weighed out and dissolved in 200 ml of distilled water.

b) Once the prilocaine was dissolved, the solution was added to the separatory funnel.

c) In a small beaker, 30 g of sodium hydroxide pellets was added to 50 ml of water. This solution was then added to the prilocaine mixture in the funnel, and allowed to stand for 30 minutes.

d) After 30 minutes had elapsed, the bottom layer was decanted into a beaker. This solution was saved. The top layer was saved in a 250 ml beaker. Step C was repeated with the bottom layer. Again, the bottom layer was decanted and the top layer saved. The top layer was added to the same 250 ml beaker with the previous top layer.

e) 120 g of lidocaine was added to the 250 ml beaker and mixed thoroughly.

f) 8 g of dibucaine and 5 g of phenylephrine.HCl were weighed out. These powders were placed into a glass mortar and pestle and triturated. Then, 5 ml of ethanol was added to the powders and mixed until dissolved.

g) The product of step f) was added to the lidocaine/prilocaine mixture.

h) Once this solution was clear, the final weight was obtained.

i) The weight of the mixture was subtracted from 800 in order to determine the amount of petrolatum needed.

j) The petrolatum and the mixture were placed in a vessel of sufficient size and mixed thoroughly. The mixture had less than 1% water.

k) The mixture was dispensed into 1 oz tubes. The approximate shelf life was found to be about 12 months.

EXAMPLE 2

Method of application of the formulation to the skin:

a) the skin was thoroughly de-fatted using 70% isopropyl alcohol or acetone.

b) a thin layer of the product was applied using a finger or a cotton tipped applicator.

c) the patient rested for 30 to 45 minutes while waiting for the anesthetic to take effect. On thick skin such as arms and legs, the patient waited for one hour. The patient experienced desensitization and good anesthetization.

The duration of desensitization was found to vary with the amount of product applied and the length of the waiting period. The minimum time reported was 90 minutes and the longest reported was six hours. The average desensitization period reported was 180 minutes.

With respect to the above description then, it is to be realized that the optimum relationships for the components of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact formulation and operation shown and described, and accordingly, all suitable modifications and equivalents may be resorted to, falling within the scope of the invention.

Now that the invention has been described,
What is claimed is:

1. A local topical, transdermal anesthetic formulation, comprising a eutectic mixture of lidocaine and prilocaine in a weight ratio of from about 15:1 to about 2:1 in a lipophilic base.

2. A formulation as in claim 1, wherein said weight ratio of lidocaine to prilocaine is from about 8:1 to about 2.5:1.

3. A formulation as in claim 1, wherein said weight ratio of lidocaine to prilocaine is about 3:1.

4. A formulation as in claim 1, further comprising dibucaine from 0 to 1% by weight of the total formulation.

5. A formulation as in claim 1, further comprising a vasoconstrictor.

6. A formulation as in claim 5, wherein said vasoconstrictor is a sympathomimetic amine.

7. A formulation as in claim 6, wherein said sympathomimetic amine is phenylephrine.

8. A formulation as in claim 7, wherein said phenylephrine is present in an amount of from 0 to 2% by weight based upon the total weight of said formulation.

9. A formulation as in claim 1, wherein said lipophilic base is a petroleum product in which said eutectic mixture is completely miscible.

10. A formulation as in claim 1, wherein said lipophilic base is a higher aliphatic alcohol of 8–18 carbon atoms, or an ester thereof.

11. A formulation as in claim 1, wherein said lidocaine comprises from 10% to 20% by weight, and said prilocaine comprises 1% to 5% by weight, of the total weight said formulation.

12. A formulation as in claim 1, wherein said lipophilic base comprises from 70% to 89% by weight of said formulation.

13. A method of obtaining local anesthesia in mammals by way of topical, transdermal application, said method comprising administering a formulation comprising an eutectic mixture of lidocaine and prilocaine in a weight ratio of from about 15:1 to about 2:1 in a lipophilic base.

14. A method as in claim 13, wherein said formulation further comprises dibucaine.

15. A method as in claim 13, wherein said formulation further comprises a vasoconstrictor.

16. A method as in claim 15, wherein said vasoconstrictor is a sympathomimetic amine.

17. A method as in claim 16, wherein said sympathomimetic amine is phenylephrine.

18. A formulation as in claim 17, wherein said lidocaine and prilocaine are present in a weight ratio of from about 15:1 to about 2:1.

19. A local topical, transdermal anesthetic formulation, comprising a eutectic mixture of at least one first pharmaceutically active anesthetic and at least one second pharmaceutically active anesthetic in a ratio of about 15:1 to about 2:1 in a lipophilic base, wherein said at least one first pharmaceutically active anesthetic is selected from the group consisting of benzocaine, lidocaine, bupivacaine, dibucaine, mepivacaine, etidocaine, tetracaine, butanilicaine and trimecaine said at least one second pharmaceutically active anesthetic is selected from the group consisting of prilocaine, tetracaine, butanilicaine and trimecaine, and said at least one first pharmaceutically active anesthetic is different than said at least one second pharmaceutically active anesthetic.

20. A local topical, transdermal anesthetic formulation as in claim 19, comprising at least one of lidocaine and prilocaine.

* * * * *